United States Patent [19]

Leung

[11] Patent Number: 5,198,334
[45] Date of Patent: Mar. 30, 1993

[54] PROTECTION OF NATURAL KILLER CELL CYTOLYTIC ACTIVITY IN PERIPHERAL BLOOD MONONUCLEAR CELLS

[75] Inventor: Kam H. Leung, Brookhaven, Pa.

[73] Assignee: Terumo Corporation, Tokyo, Japan

[21] Appl. No.: 383,222

[22] Filed: Jul. 21, 1989

[51] Int. Cl.$^5$ .................... A01N 1/02; A61K 35/14; C12N 5/08
[52] U.S. Cl. .................... 435/2; 435/240.1; 435/240.2; 435/240.21; 435/240.25; 514/885; 604/4; 604/5; 604/6
[58] Field of Search .................... 435/2, 240.1, 240.2, 435/240.21, 240.23, 240.25; 424/93; 514/885; 604/4, 5, 6

[56] References Cited

U.S. PATENT DOCUMENTS

| | | | |
|---|---|---|---|
| 4,752,602 | 6/1988 | Lipsky et al. | 514/19 |
| 4,849,329 | 7/1989 | Leung et al. | 435/2 |

OTHER PUBLICATIONS

Leung: Cancer Immunol. Immunotherap. 30: 247-253 (1989).
Leung Cancer Immunol Immunotherap 34: 31-36 (1991).
Imir et al, "Generation of Natural Killer Cells and Lymphokine-Activated Killer cells in human AB Serum or Fetal Bovine Serum", Clinical Immunology and Immunopathology V. 36, 289-296 (1985).
Restow et al, "In vitro effects of protease inhibitors on murine natural Killer cell Activity", Immunology, V. 48, pp. 1-8, 1983.
Hoyer et al. (1986), *Cancer Research* 46:2834-2838.
Thiele et al. (1985), *J. Immunol.* 144:786-793.
Leung, *Lymphokine Research*, vol. 6, Abstract No. 1718 (1987).

*Primary Examiner*—David L. Lacey
*Assistant Examiner*—Phillip Gambel
*Attorney, Agent, or Firm*—Burns, Doane, Swecker & Mathis

[57] ABSTRACT

Leucinol, phenylalaninol and benzamide protect against loss of Natural Killer activity when Peripheral Blood Mononuclear Cells are treated with an ester of an amino acid or dipeptide or an amide of an amino acid prior to incubation with IL-2 to generate Lymphokine-Activated Killer activity.

19 Claims, No Drawings

PROTECTION OF NATURAL KILLER CELL CYTOLYTIC ACTIVITY IN PERIPHERAL BLOOD MONONUCLEAR CELLS

BACKGROUND OF THE INVENTION

Natural killer (NK) cells and lymphokine-activated killer (LAK) cells have been implicated in immunosurveillance against tumor cells and allograft rejection (T. Barlozzari, C. W. Reynolds, and R. B. Herberman, *J. Immunol.*, 131, 1024, 1983; A. A. Rayner, E. A. Grimm, M. T. Lotze, E. W. Chu, and S. A. Rosenberg, *Cancer*, 55, 1327, 1985). These effector cells also play a role in the regulation of immune responses (R. B. Herberman and J. R. Ortaldo, *Science*, 214, 24, 1981) and the control of viral and bacterial infections (R. M. Natuk and R. M. Welsh, *J. Immunol.*, 138, 877, 1987; Weinhold et al. *Lancet*, Apr. 23, 902-904 (1988)). Therefore, it is of potential importance to be able to efficiently prepare functional NK cells for adoptive transfer immunotherapy in humans.

It was shown that monocytes interfere with the activation of LAK activity by IL-2. L-leucine methyl ester (LME) and L-phenylalanine methyl ester (PME) were shown to remove monocytes from human peripheral blood mononuclear cells (PBMC). LME was also shown to deplete NK activity and NK cells (M. Hoyer, T. Meineke, W. Lewis, B. Zwilling, and J. Rinehart, *Cancer Res.*, 46, 2834, 1986; D. L. Thiele and P. E. Lipsky, *J. Immunol.*, 134, 786, 1985; Lipsky and Thiele, U.S. Pat. No. 4,752,602).

Monocytes have also been removed by their adherence to nylon-wool columns or by centrifugal elutriation in order to generate LAK cells at high cell density. However, these procedures for monocyte removal are tedious and complicated. Some LAK cell precursors may also adhere to the nylon-wool columns. Therefore, we have employed PME, at a concentration of about 1 to 5 mM, as a single step for monocyte depletion. We were able to generate LAK from PME-treated cells. We have shown that depletion of monocytes by PME allows generation of LAK cells by rIL-2 at a cell density of $5 \times 10^6$/mL or higher (Leung, K. H., *Lymphokine Research*, 6, Abstract #1718, 1987; European patent application 87107755.8, published Dec. 2, 1987, and U.S. Pat. No. 4,849,329.

Depletion of monocytes by PME, as with LME, also diminished the NK activity of the cells. However, whereas inhibition of NK activity by LME was irreversible, with PME, the NK activity is recovered within 18 hr by incubation of the cells in medium supplemented with FCS or IL-2 at 37° C. This recovery process may not, however, be acceptable for infusion to a patient in an adoptive transfer therapy protocol. We have, therefore, studied the removal of monocytes using amino acid lower alkyl esters in the presence of other amino acid analogs to determine whether these analogs may protect NK cell activity from inhibition by the amino acid lower alkyl ester.

SUMMARY OF THE INVENTION

We have discovered that three amino acid analogs—phenylalaninol (PheOH), benzamidine, and leucinol (LeuOH)—inhibit loss of NK activity in PBMC treated with LME or PME. PheOH and benzamidine did not interfere with monocyte depletion by PME or LME, whereas LeuOH prevented monocyte depletion as well as NK depletion by PME and LME. We have also discovered that LAK activity can be generated in PBMC which have been treated with LME or PME and PheOH, LeuOH, or benzamidine. It was surprising that a high level of LAK activity could be generated in PBMC treated with LME or PME and LeuOH, since LeuOH prevented monocyte depletion by both LME and PME.

It is expected that these findings will be equally applicable to esters and amides of other amino acids and dipeptides known to reversibly or irreversibly deplete monocytes from PBMC. The amino acid analogs can be used to protect against loss of NK activity not only in PBMC but also in peripheral blood lymphocytes (PBL) derived therefrom, e.g., by treatment of PBMC with nylon wool or centrigugal elutriation to deplete monocytes.

Thus, in one aspect our invention is a method of generating LAK cell activity in peripheral blood mononuclear cells (RBMC) or peripheral blood lymphocytes (PBL) derived therefrom while retaining natural killer (NK) cell activity which comprises:

(a) treating the PBMC or PBL with (i) a lower alkyl ester of an amino acid or dipeptide selected from the group consisting of leucine, alanine, aspartic acid, cysteine, glutamic acid, glutamine, phenylalanine, proline, tyrosine, tryptophan, valine and dipeptides composed of residues of one or two of said amino acids, or an amide of an amino acid selected from the group consisting of leucine, isoleucine, phenylalanine and valine, or a pharmaceutically acceptable salt of said ester or amide, and (ii) a member of the group consisting of benzamidine, phenyalaninol and leucinol, then (b) culturing the cells in growth medium containing interleukin-2 to produce LAK cells which are cytotoxic for NK-resistant tumor cells.

In another aspect, this invention is a method of depleting monocytes from peripheral blood mononuclear cells (PBMC) while retaining natural killer (NK) cell activity in the cells which comprises treating the PBMC with (a) a lower alkyl ester of an amino acid or dipeptide or an amide of an amino acid as defined above, or a pharmaceutically acceptable salt of said ester or amide, and (b) a member of the group consisting of benzamidine and phenyalaninol.

In another aspect, the invention is a method of inhibiting monocyte depletion and loss of NK activity upon treating PBMC with a lower alkyl ester of an amino acid or dipeptide or an amide of an amino acid as defined above, or a pharmaceutically acceptable salt of said ester or amide, which comprises simultaneously treating the cells with leucinol.

DETAILED DESCRIPTION

The three amino acid analogs used in this invention are represented by the following structural formulae:

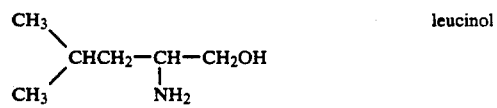
leucinol

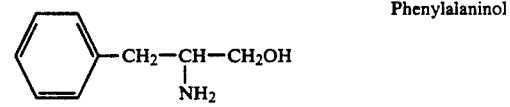
Phenylalaninol

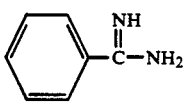

Benzamidine

As mentioned above, European patent application 87107775.8, published Dec. 2, 1987, and corresponding U.S. Pat. No. 4,849,329, disclose the treatment of PBMC or PBL with lower alkyl esters of certain amino acids to enhance LAK activation. The conditions used in this invention for treatment of PBMC and for LAK activation are the same as described in the European application 87107775.8 and U.S. Pat. No. 4,849,329 the disclosures of which are incorporated herein. PBMC for use in the invention can be obtained by Ficoll-Hypaque density gradient separation as described in the above applications or without Ficoll-Hypaque separation, as disclosed in U.S. Pat. No. 4,808,151, issued Feb. 28, 1989, the disclosure of which is also incorporated herein. The PBMC are washed, optionally treated by conventional techniques to deplete monocytes, as described in the incorporated applications, and suspended in suitable medium at a concentration in the range of about $1 \times 10^6$ to $2 \times 10^7$ cells per mL.

The PBMC or resulting PBL are then treated with the amino acid ester or amide at a concentration in the range of about 1 mM to 5 mM and with benzamidine, PheOH or LeuOH at a concentration in approximately the same range. Concentrations are based on the total volume of PBMC suspension and solution of ester or amide and analog. Contacting is carried out at ambient temperature, preferably 20°–25° C. for a period of at least 15 minutes, preferably about 20–40 minutes.

The esters used in this invention can be not only those disclosed in the incorporated applications which reversibly inhibit NK activity but also esters of amino acids and dipeptides, such as LME and leucyl leucine methyl ester (LLME) which irreversibly inhibit NK activity. The dipeptides are disclosed in Lipsky and Thiele U.S. Pat. No. 4,752,602, the disclosure of which is also incorporated herein. Pharmaceutically acceptable salts of the esters and amides can also be used; preferred salts are the hydrogen chloride and hydrogen bromide salts.

The suspension of PBMC or PBL is then cultured for an incubation period of about 2 to 7 days at 35° to 39° C., preferably 37° C., in presence of about 4–7% $CO_2$. Culturing is carried out at a cell concentration in the range of about $1 \times 10^6$ to $2 \times 10^7$, preferably $5 \times 10^6$ to $1 \times 10^7$ cells per mL, in medium containing IL-2 in concentration of about 150 to 1500 pM, preferably 1000–2000 pM. Culturing can be performed in conventional containers, such as T-flasks, but is preferably performed in closed, gas permeable sterile bags such as Du Pont's SteriCell TM cell culture bags. Culturing under these conditions generates LAK cells, a population of cells which are able to lyse tumor cells which are resistant to lysis by NK cells.

LAK cells prepared by this invention are used in adoptive immunotherapy in the manner described in the incorporated applications 87107755.8 and U.S. Pat. No. 4,849,329.

In the Examples which follow, a 4 hour 51Cr release assay was used to measure cytotoxicity of LAK cells for tumor cells. Tumor cells at a concentration of about $2 \times 10^6$ to $10 \times 10^6$ were incubated with 50 μCi of $Na_2{}^{51}CrO_4$ in 0.4 mL of Tris-phosphate buffered saline for 1 hour at 37° C. The cells are washed 4 times with RPMI 1640 containing 5% or 10% fetal calf serum (FCS) and resuspended to $10^5$ cells/mL in RPMI-20% FCS or RPMI 10% FCS. The effector cells (LAK cells) are suspended to various concentrations and 0.1 mL is added to wells in round bottom microtiter plates. The $^{51}Cr$ labelled target cells (0.1 mL) are added to all wells and the plates are centrifuged at 200 xg for 5 minutes. After 4 hours of incubation at 37° C., the plates are centrifuged again and 0.1 mL of resulting supernatant is removed from each well and counted in a gamma counter. Percent cytotoxicity is calculated from the following formula:

$$\% \text{ cytotoxicity} = \frac{\text{experiment cpm} = \text{spontaneous cpm}}{\text{total cpm} - \text{spontaneous cpm}} \times 100$$

Each variable is tested in triplicate and the resulting data is expressed as % cytotoxicity or lysis. This cytotoxicity test is further described in "Selected Methods in Cellular Immunology", Mishell and Shiigi, eds., 124–137, W. H. Freeman and Co., San Francisco (1980).

EXAMPLE 1

We have studied the effect of PheOH and benzamidine on monocyte depletion, NK activity, and LAK activation by IL-2 of PBMC treated with PME. PBMC were treated with 5 mM PME in the presence or absence of PheOH and benzamidine. The PME-treated PBMC were analyzed for the % of monocytes by Giemsa staining and NK activity against K562 target cells, and were then cultured at $1 \times 10^7$/mL with media containing rIL-2 for 3–4 days. LAK cell activity was then measured against $^{51}Cr$-labeled Raji target cells.

The experimental results are shown in Table 1. PME alone depleted monocytes from 50% to 3%. PheOH and benzamidine had little effect on monocyte depletion by themselves and they did not interfere with the monocyte depletion by PME. However, as shown in Table 1, both PheOH and benzamidine prevented the inhibition of NK activity induced by PME treatment of PBMC. Moreover, the presence of PheOH or benzamidine also did no interfere with the LAK activation by IL-2 at high cell density, which is enhanced by PME treatment.

TABLE 1

Effect of PheOH and Benzamidine in Combination with PME on Monocyte Depletion, NK Activity, and LAK Activation

| | | [PME], mM | |
|---|---|---|---|
| | | 0 | 5 |
| | | % Monocytes | |
| [PheOH], mM | 0 | 50 | 3 |
| | 1 | 45 | 1 |
| | 2.5 | 46 | 2 |
| | 5 | 47 | 1 |
| [benzamidine], mM | 1 | 52 | 3 |
| | 2.5 | 49 | 2 |
| | 5 | 42 | 1 |
| | | % Lysis, NK activity (Day 0) (E:T ratio, 20:1 against K562) | |
| [PheOH], mM | 0 | 27 | 6 |
| | 1 | 28 | 12 |
| | 2.5 | 25 | 20 |
| | 5 | 23 | 18 |
| [benzamidine], mM | 1 | 28 | 15 |
| | 2.5 | 28 | 22 |
| | 5 | 26 | 22 |
| | | % Lysis, LAK activity | |

TABLE 1-continued

Effect of PheOH and Benzamidine in
Combination with PME on Monocyte Depletion,
NK Activity, and LAK Activation

|  | | (E:T ratio, 20:1 against Raji) | |
|---|---|---|---|
| [PheOH], mM | 0 | 7 | 58 |
|  | 1 | 20 | 61 |
|  | 5 | 10 | 62 |
| [benzamidine], mM | 1 | 18 | 54 |
|  | 5 | 19 | 53 |

EXAMPLE 2

PBMC were treated with 5 mM PME or 5 mM LME in the presence or absence of 5 mM LeuOH or PheOH. The effect of this treatment of the PBMC on the % of monocytes, NK activity against K562 target cells, and the LAK activity against Raji target cells following culture for 3 days in the presence of IL-2, are shown in Table 2. PME or LME was able to deplete monocytes. LeuOH was able to prevent the monocyte depletion by PME or LME. On the other hand, PheOH did not prevent the monocyte depletion by PME or LME. PME had little effect on the large granular lymphocytes (LGL) as measured by fluorescence activated cell sort (FACS) analysis, but inhibited NK activity against K562. On the other hand, LME depleted LGL and NK activity. LeuOH prevented the inhibitory actions of LME on LGL and NK activity. PheOH could prevent the inhibitory effects on NK activity by PME, but only partially prevented the inhibitory effects on NK activity by LME. LeuOH and PheOH had little adverse effect on enhanced LAK activation by PME. Moreover, LeuOH and PheOH reversed the inhibitory effect of LME on LAK activation.

TABLE 2

Protective Effect of PheOH
and LeuOH NK Activity

|  | % LueM3 (a) | % Leu19 (b) | NK Activity (c) | LAK Activity (d) |
|---|---|---|---|---|
| Control | 21 | 14 | 54 | 10 |
| PME | 3 | 12 | 17 | 60 |
| LME | 2 | 3 | 0 | 0 |
| PME/LeuOH | 24 | 16 | 51 | 52 |
| LME/LeuOH | 25 | 15 | 57 | 47 |
| PME/PheOH | 2 | 11 | 40 | 50 |
| LME/PheOH | 5 | 10 | 20 | 31 |

(a) Monocyte content was determined by FACS using LeuM3 antibody against monocytes.
(b) NK cells were assessed by FACS using Leu19 antibody against NK cells.
(c) NK activity was determined on Day 0 at an E:T ratio of 50:1 using K562 targets. Numbers are % lysis.
(d) LAK activity was assessed at a E:T ratio of 20:1 against Raji target cells, after cells were incubated at 1 × 10⁷ cells/mL with 10 U/mL rIL-2 for 3 days. Numbers are % lysis.

What is claimed is:

1. A method of preparing peripheral blood mononuclear cells (PBMC) or peripheral blood lymphocytes (PBL) derived therefrom for use in generating LAK cells while retaining natural killer (NK) cell activity in the cells which comprises treating the PBMC or PBL in vitro with
   (a) a lower alkyl ester of an amino acid or dipeptide selected from the group consisting of leucine, alanine, aspartic acid, cysteine, glutamic acid, glutamine, phenylalanine, proline, tyrosine, tryptophan, valine and dipeptides composed of residues of one or two of said amino acids, or an amide of an amino acid selected from the group consisting of leucine, isoleucine, phenylalanine and valine, or a pharmaceutically acceptable salt of said ester or amide, and
   (b) a member of the group consisting of benzamidine, phenylalaninol and leucinol.

2. Method of claim 1 wherein in step (a) the PBMC or PBL at a concentration in the range of about $1 \times 10^6$ to $2 \times 10^7$ cells per mL are treated with the amino acid ester or amide at a concentration in the range of about 1 to 5 mM and with benzamidine, phenylalaninol or leucinol at a concentration in the range of about 1 to 5 mM.

3. Method of claim 2 wherein the PBMC or PBL are treated with phenylalanine methyl ester or phenylalanine amide.

4. Method of claim 3 wherein the PBMC or PBL are treated with phenylalaninol.

5. Method of claim 3 wherein the PBML or PBL are treated with leucinol.

6. Method of claim 3 wherein the PBMC or PBL are treated with benzamidine.

7. Method of claim 2 wherein the PBMC or PBL are treated with leucine methyl ester or leucine amide.

8. A method of depleting monocytes from peripheral blood mononuclear cells (PBMC) while retaining natural killer (NK) cell activity in the cells which comprises treating the PBMC in vitro with
   (a) a lower alkyl ester of an amino acid or dipeptide selected from the group consisting of leucine, alanine, aspartic acid, cysteine, glutamic acid, glutamine, phenylalanine, proline, tyrosine, tryptophan, valine and dipeptides composed of residues of one or two of said amino acids, or an amide of an amino acid selected from the group consisting of leucine, isoleucine, phenylalanine and valine, or a pharmaceutically acceptable salt of said ester or amide, and
   (b) a member of the group consisting of benzamidine and phenylalaninol.

9. Method of claim 8 wherein the PBMC at a concentration in the range of about $1 \times 10^6$ to $2 \times 10^7$ cells per mL are treated with the amino acid ester or amide at a concentration in the range of about 1 to 5 mM and with benzamidine or phenylalaninol at a concentration in the range of about 1 to 5 mM.

10. Method of claim 9 wherein in step (a) the PBMC or PBL are treated with phenylalanine methyl ester or phenylalanine amide.

11. Method of claim 10 wherein in step (a) the PBMC or PBL are treated with phenylalaninol.

12. Method of claim 10 wherein in step (a) the PBMC or PBL are treated with benzamidine.

13. Method of claim 9 wherein in step (a) the PBMC or PBL are treated with leucine methyl ester or leucine amide.

14. Method of claim 13 wherein in step (a) the PBMC or PBL are treated with phenylalaninol.

15. Method of claim 13 wherein in step (a) the PBMC or PBL are treated with benzamidine.

16. A method of inhibiting monocyte depletion in vitro treating PBMC with a lower alkyl ester of an amino acid or dipeptide selected from the group consisting of leucine, alanine, aspartic acid, cysteine, glutamic acid, glutamine, phenylalanine, proline, tyrosine, tryptophan, valine and dipeptides composed of residues of one or two of said amino acids, or an amide of an amino acid selected from the group consisting of leucine, isoleucine, phenylalanine and valine, or a pharmaceutically acceptable salt of said ester or amide, which comprises simultaneously treating the cells with leucinol.

17. Method of claim 16 wherein the PBMC at a concentration in the range of about $1 \times 10^6$ to $2 \times 10^7$ cells per mL are treated with the amino acid ester or amide at a concentration in the range of about 1 to 5 mM and with leucinol at a concentration in the range of about 1 to 5 mM.

18. Method of claim 17 wherein the PBMC are treated with phenylalanine methyl ester or phenylalanine amide and leucinol.

19. Method of claim 17 wherein the PBMC are treated with phenylalanine methyl ester or leucine amide and leucinol.

* * * * *

UNITED STATES PATENT AND TRADEMARK OFFICE
CERTIFICATE OF CORRECTION

PATENT NO. : 5,198,334
DATED : March 30, 1993
INVENTOR(S) : Kam H. LEUNG

It is certified that error appears in the above-identified patent and that said Letters Patent is hereby corrected as shown below:

In Column 2, line 16, delete "centrigugal" and insert -- centrifugal --.

In Column 2, line 20, delete "RBMC" and insert -- PBMC --.

In Column 3, line 63, delete "51Cr" and insert -- $^{51}$Cr --.

In Column 4, line 15, delete "experiment" and insert -- experimental --.

In Column 6, line 18, delete "PBML" and insert -- PBMC --.

In Column 6, line 61, after "vitro", insert -- upon --.

Signed and Sealed this

Fifteenth Day of February, 1994

Attest:

BRUCE LEHMAN

Attesting Officer

Commissioner of Patents and Trademarks